(12) United States Patent
Salomon et al.

(10) Patent No.: US 7,368,423 B1
(45) Date of Patent: May 6, 2008

(54) COMPOSITION AND METHOD FOR TREATING CHRONIC ALLOGRAFT REJECTION

(75) Inventors: Daniel R. Salomon, San Diego, CA (US); Donald V. Cramer, Agoura Hills, CA (US)

(73) Assignee: The Scripps Research Institute, La Jolla, CA (US)

( * ) Notice: Subject to any disclaimer, the term of this patent is extended or adjusted under 35 U.S.C. 154(b) by 217 days.

(21) Appl. No.: 10/006,562

(22) Filed: Dec. 5, 2001

(51) Int. Cl.
*A61K 38/00* (2006.01)
*A61K 38/12* (2006.01)

(52) U.S. Cl. .............................. 514/9; 514/11; 530/317

(58) Field of Classification Search .................... 514/9, 514/11; 530/317
See application file for complete search history.

(56) References Cited

OTHER PUBLICATIONS

Nawrocki et al., Transplantation Proceedings, vol. 28, No. 6, pp. 3538-3539, 1996.*
Schmid et al., Eur. Surg. Res., vol. 30, pp. 61-68, 1998.*
Cramer et al., Transplantation Proceedings, vol. 29, p. 616, 1997.*
Cramer, D.V. et al., "2-Chlorodeoxyadenosine in Combination With Cyclosporine Inhibits the Development of Transplant Arteriosclerosis in Rat Cardiac Allografts," *Transplantation Proceedings*, 29:616 (1997).
Demetris, A.J. et al., "Analysis of Chronic Rejection and Obliterative Arteriopathy," *American Journal of Pathology*, vol. 150, No. 2: 563-578 (1997).
Häyry, P., "Pathophysiology of Chronic Rejection," *Transplantation Proceedings*, vol. 28, No. 6, Suppl 1, 7-10 (1996).
Häyry, P. et al., "Towards Understanding the Pathophysiology of Chronic Rejection," *Clin Investig* 70:780-90 (1992).
Nawrocki, G. et al., "Prolongation of Cardiac Allograft Survival in Rats Following Combination Treatment With 2-Chloro-2'-Deoxyadenosine and Cyclosporine," *Transplantation Proceedings*, vol. 28, No. 6 pp. 3538-3539 (1996).
Nowaczyk, M. et al., "2-Chlorodeoxyadenosine: Lack of Synergism with Cyclosporine A and Tacrolimus (FK506)," *Arch Immunol Ther Exp.* Warsz 43(5-6):329-32 (1995).
Orosz, C. G. et al., "Chronic Remodeling Pathology in Grafts," *Current Opinion in Immunology* 9:676-680 (1997).
Rao, V. K., "Posttransplant Medical Complications," *Surgical Clinics of North America* vol. 78 No. 1: 113-132 (1998).
Schmid, T. et al., "2-Chlorodeoxyadenosine in Combination with Cyclosporine Prevents Rejection After Allogenic Small Bowel Transplantation" *Transplantation Proceedings*, vol. 26 No. 3: 1614 (1994).
Schmid, T. et al., "2-Chlorodeoxyadenosine in Combination with Low-Dose Cyclosporine Prevents Rejection After Allogenic Heart and Liver Transplantation in the Rat," *Eur Surg Res* 30:61-68 (1998).
Schmid, T. et al., "Histologic Pattern of Small Bowel Allograft Rejection in the Rat," *Gastroenterology* vol. 96 No. 6, pp. 1529-1532 (1989).
Wu, G.D. et al., "FK 506 Inhibits the Development of Transplant Arteriosclerosis," *Transplantation Proceedings* vol. 23, No. 6 pp. 3272-3274 (1991).
Häyry, P. et al., "Molecular Biology of Chronic Rejection and Predictive Value of Biopsies." In *Solid Organ Transplant Rejection Mechanisms, Pathology, and Diagnosis*, Kim Solez et al., eds. (NY: Marcel Dekker, Inc.), pp. 77-106 (1996).
Supplementary European Search Report Dated Feb. 8, 2005, Application No. EP 02 80 4721.
Aranda JM Jr, Hill J., Cardiac transplant vasculopathy. Chest. Dec. 2000;118(6):1792-800.
Bueno V, Pestana JO. The role of CD8+ T cells during allograft rejection. Braz J Med Biol Res. Nov. 2002;35(11):1247-58.
Chandraker A, Azuma H, Nadeau K, Carpenter CB, Tilney NL, Hancock WW, Sayegh MH. Late blockade of T cell costimulation interrupts progression of experimental chronic allograft rejection.J Clin Invest. Jun. 1, 1998;101(11):2309-18.
Choy JC, Kerjner A, Wong BW, McManus BM, Granville DJ. Perforion mediates endothelial cell death and resultant transplant vascular disease in cardiac allografts. Am J Pathol. Jul. 2004;165(1):127-33.
Demetris, et al., Pathophysiology of Chronic Allograft Rejection CME, Mar. 29, 2000, http://www.medscape.com/viewprogram/336_pnt, visited Jul. 21, 2005, p. 1-71.
Fischbein MP, Yun J, Laks H, Irie Y, Fishbein MC, Bonavida B, Ardehali A. Role of CD8+ lymphocytes in chronic rejection of transplanted hearts. J Thorac Cardiovasc Surg. Apr. 2002;123(4):803-9.
Grieb P, Ryba M, Janczewski W, Sawicki J, Jagielski J, Andrychowski J. 2-Chloro-2'-deoxyadenosine (2-CdA) combined with cyclosporine A successfully prevents rejection of fetal brain stem allograft in rabbits. Arch Immunol Ther Exp (Warsz). 1994;42(1):43-6.
He C, Schenk S, Zhang Q, Valujskikh A, Bayer J, Fairchild RL, Heeger PS. Effects of T cell frequency and graft size on transplant outcome in mice. J Immunol. Jan. 1, 2004;172(1):240-7.
Hollenberg SM, Klein LW, Parrillo JE, Scherer M, Burns D, Tamburro P, Oberoi M, Johnson MR, Costanzo MR. Coronary endothelial dysfunction after heart transplantation predicts allograft vasculopathy and cardiac death. Circulation. Dec. 18, 2001;104(25):3091-6.
Kobashigawa J. What is the optimal prophylaxis for treatment of cardiac allograft vasculopathy? Curr Control Trials Cardiovasc Med. 2000;1(3):166-171.

(Continued)

*Primary Examiner*—Jon Weber
*Assistant Examiner*—Abdel A Mohamed
(74) *Attorney, Agent, or Firm*—Mirick, O'Connell, DeMallie & Lougee, LLP; Roger P. Zimmerman

(57) ABSTRACT

The invention provides a composition and a method for preventing or ameliorating the causes of chronic allograft rejection of a donor organ by a transplant recipient. The method includes concomitant administration to the allograft recipient of therapeutically effective amounts of cyclosporin and 2-chlorodeoxyadenosine. The composition comprises a combination of these two immunosuppressive drugs in therapeutically effective amounts suitable for the practice of the method.

11 Claims, 4 Drawing Sheets

OTHER PUBLICATIONS

Knoop C, Haverich A, Fischer S. Immunosuppressive therapy after human lung transplantation. Eur Respir J. Jan. 2004;23(1):159-71.

Koh KP, Wang Y, Yi T, Shiao SL, Lorber MI, Sessa WC, Tellides G, Pober JS. T cell-mediated vascular dysfunction of human allografts results from IFN-gamma dysregulation of NO synthase. J Clin Invest. Sep. 2004;114(6):846-56.

Kouwenhoven EA, IJzermans JN, de Bruin RW. Etiology and pathophysiology of chronic transplant dysfunction. Transpl Int. 2000;13(6):385-401.

Mehra MR, Ventura HO, Smart FW, Stapleton DD, Collins TJ, Ramee SR, Murgo JP, White CJ. New developments in the diagnosis and management of cardiac allograft vasculopathy. Tex Heart Inst J. 1995;22(2):138-44.

Oberhuber G, Schmid T, Thaler W, Kaltenbacher A, Schirmer M, Liliemark J, Herbst P, Geisen F, Margreiter R, Konwalinka G. Evidence that 2-chlorodeoxyadenosine in combination with cyclosporine prevents rejection after allogeneic small bowel transplantation. Transplantation. Sep. 27, 1994;58(6):743-5.

Shapiro R. Low toxicity immunosuppressive protocols in renal transplantation. Keio J Med. Mar. 2004;53(1):18-22.

Shi C, Lee WS, He Q, Zhang D, Fletcher DL Jr, Newell JB, Haber E. Immunologic basis of transplant-associated arteriosclerosis. Proc Natl Acad Sci U S A. Apr. 30, 1996;93(9):4051-6.

Slachta CA, Jeevanandam V, Goldman B, Lin WL, Platsoucas CD. Coronary arteries from human cardiac allografts with chronic rejection contain oligoclonal T cells: persistence of identical clonally expanded TCR transcripts from the early post-transplantation period (endomyocardial biopsies) to chronic rejection (coronary arteries). J Immunol. Sep. 15, 2000:165(6):3469-83.

Adams, A.B., et al., Conventional immunosuppression and co-stimulation blockade. Philos Trans R Soc Lond B Biol Sci. May 29, 2001;356(1409):703-5.

Iwakoshi NN, et al., Skin allograft maintenance in a new synchimeric model system of tolerance. J Immunol. Dec. 1. 2001;167(11):6623-30.

Sho, M., et al., New insights into the interactions between T-cell costimulatory blockade and conventional immunosuppressive drugs. Ann Surg. Nov. 2002;236(5):667-75.

\* cited by examiner

COMPOSITION AND METHOD FOR TREATING CHRONIC ALLOGRAFT REJECTION

This invention relates to the field of organ transplantation in humans and animals. Specifically, the invention relates to a composition and a method for preventing or ameliorating chronic rejection of the donor organ by the transplant recipient.

BACKGROUND OF THE INVENTION

A significant problem in organ transplantation today is the failure of current immunosuppressive strategies to significantly reduce the risk of rejection in kidney, heart, lung and pancreas transplantation more than one to two years post transplant. As a result, the tremendous gains made in the rates of one to two year survival of the transplanted organ over the last decade are largely lost at five to ten years post transplant when the majority of transplant patients, especially those receiving cadaver donor organs, have lost function in the transplanted organ.

Pathology of Allograft Rejection

There are three general stages of allograft rejection: hyperacute, acute, and chronic. In general, hyperacute rejection occurs within the first hours after transplantation. Acute rejection generally occurs in the first six to twelve months after transplantation and chronic rejection generally occurs later, usually more than one to two years post transplant.

Each stage of allograft rejection has a characteristic histopathology. Hyperacute rejection is known to be due to antibodies in the organ recipient's blood stream that react with the new organ. Hyperacute rejection results in organ failure almost immediately after transplantation.

Acute rejection is characterized by inflammation initiated by a strong T-cell based immune response to alloantigens. This T-cell based immune response can occur either directly, by cross reaction with allogeneic major histocompatibility complex (MHC) molecules, or indirectly, by the more usual route of reaction with allogeneic peptide fragments bound to host MHC molecules on antigen-presenting cells or allogeneic target cells. T-cells not only initiate the immune response, but also mediate antigen-specific effector responses. In addition, T-cells secrete soluble factors to regulate the activity of other leukocytes. For example, activated T-helper cells produce interleukins, gamma interferon and leukotrienes. This cascade of immunoregulators stimulates the attack of cytotoxic T-lymphocytes on the allograft. In irreversible rejection fatal to the allograft, these cytotoxic lymphoid cells eventually give way to larger numbers of mononuclear phagocytes and thrombocytes. The end result of the binding of thrombocytes to the allograft vascular endothelial cells is reduced blood flow, microvascular thrombosis and necrosis. Hayry, P. et al. *Clin Investig* 70:780-90 (1992).

In contrast to the endovascular pathology of acute rejection, chronic rejection has persistent perivascular inflammation as its most prominent feature. Often, this perivascular inflammation is accompanied by relatively low levels of lymphoid activity and arteriosclerosis of the allograft. However, compared to ordinary arteriosclerosis, which is usually defined by focal and eccentric intimal thickening, the common form of allograft arteriosclerosis is concentric and generalized intimal thickening where smooth muscle cells in the vascular intima are intermingled with some inflammatory T cells and macrophages. Hayry, P. et al. *Clin Investig* 70:780-90 (1992). The allograft arteriosclerosis of chronic rejection affects all intramural arteries to the level of arterioles. Other common features of chronic rejection are thinning of the vascular media and focal breaks in the internal elastic lamina.

Evidence from studies of cytokine production also supports the hypothesis that chronic rejection that is characterized by perivascular inflammation is the result of a low level immune response, that in turn induces persistent minimal damage to the allograft vascular endothelium. In response to this damage to the allograft vessels, the endothelial cells secrete growth factors, such as platelet-derived growth factor, epidermal growth factor, basic fibroblast growth factor, and transforming growth factor-beta. These growth factors stimulate the proliferation of smooth muscle cells and the migration of myocytes from the media into the intima thereby forming the arteriosclerotic lesion. Häyry, P. et al. *Clin Investig* 70:780-90 (1992).

Pharmaceutical Treatment of Allograft Rejection

A number of immunosuppressant drugs are known and have used for the treatment of allograft rejection. These include, for example, cyclosporin, azathioprine, FK-506, methylprednisolone, deoxypergualin, rapamycin, and mycophenylate. Today, cyclosporin (CSA) forms the basis of most immunosuppressive protocols. However, CSA's effectiveness is limited by is well known toxic side effects such as nephrotoxicity and hepatotoxicity.

In order to reduce such toxic side effects, CSA is usually combined with other immunosuppressive drugs in order to reduce the dosage of CSA to non-toxic levels. For this purpose, CSA was first combined with steroids such as methylprednisolone and later in a combination with steroids and azathioprine, which became known as triple drug therapy. However, even more potent newer immunosuppressants, such as FK-506, have been associated with toxic side effects similar to those of CSA. Schmid, T. et al. *Eur Surg Res* 30:61-68 (1998)

A relatively new drug, the purine nucleoside analogue, 2-chlorodeoxyadenosine (2-CDA), has already been used as a cytotoxic drug for the treatment of hairy cell leukemia, and autoimmune diseases such as autoimmune hemolytic anemia and multiple sclerosis. Because of its cytotoxicity to lymphocytes and monocytes, 2-CDA also possesses immunosuppressive properties. Although 2-CDA alone has no effect on allograft rejection, it is known to act synergistically with CSA to enhance the immunosuppressive effect of CSA when used in combination for the treatment of acute rejection. Schmid, T. et al. *Eur Surg Res* 30:61-68 (1998).

A number of studies have shown that the use of 2-CDA in combination with CSA may improve short-term allograft survival. One study showed that 2-chlorodeoxyadenosine, in combination with CSA reduced rejection after allogeneic small bowel transplantation in rats. Here, organ recipient rats that received a transplant of small bowel were sacrificed ten days after transplantation and the graft was examined histologically. Rats treated with a combination of 2-CDA and CSA either exhibited no evidence of graft rejection or evidence of only moderate rejection characterized by mucosal and submucosal infiltration of eosinophils and occasionally lymphocytes. However, organ recipient rats treated with either CSA or 2-CDA alone showed moderate to severe rejection including lymphocyte and polymorphonuclear granulocyte infiltration of the muscular layer and subserous fat of the graft. Schmid, T. et al. *Transplantation Proceedings*, 26: 1614 (1994).

Similar results were obtained in a second study involving rats that had received heart transplants. Heart allografts examined at 10 days post transplant revealed either no evidence of rejection or evidence of only mild rejection. The mild rejection was characterized by at least two foci of extensive perivascular or interstitial lymphocytic infiltration without myocyte necrosis, or one large focus of infiltration, including distortion of myocytes. Organ recipient rats treated with CSA alone exhibited either the same level of mild rejection or moderate rejection, which was characterized by multiple large lymphocytic infiltrates associated with distortion of myocyte architecture and/or myocyte necrosis. Host rats treated with 2-CDA alone exhibited severe rejection, which was characterized by extensive infiltrates as in moderate rejection that includes significant numbers of granulocytes and interstitial edema. Schmid, T., et al. *Eur Surg Res* 30:61-68 (1998).

Another study reported that graft survival in rats could be prolonged by the administration of CSA in conjunction with 2-CDA. Nawrocki, G., et al. *Transplantation Proceedings,* 28:3538-39 (1996). However, all animals died by 33 days post-transplant and there was no investigation into the pathology associated with the graft rejection.

Another study reported that organ recipient rats treated with 2-CDA and CSA displayed less of the pathology associated with graft rejection than rats treated with CSA alone at ninety days post transplant. Cramer, D. V. et al. *Transplantation Proceedings,* 29:616 (1997). Here, histopathological findings, including vascular intimal proliferation, perivascular fibrosis, myocardium inflammation, and myocardium fibrosis, were scored. Allograft recipients treated with CSA in combination with 2-CDA showed a reduction in the incidence and severity of vascular intimal proliferation compared to animals receiving no treatment or animals treated with CSA alone.

Although all of these studies suggest the administration of 2-CDA with CSA may limit acute allograft rejection and thus be beneficial in the improvement of short term graft survival rates, none of the studies have disclosed or suggested efficacious treatment of chronic allograft rejection.

Accordingly, what is needed is an improved method of preventing or ameliorating chronic allograft rejection, including a method of reducing the associated arteriosclerosis in human and animal allograft transplant recipients. Improved pharmaceutical compositions suitable for preventing or reducing chronic allograft rejection allograft recipients are also needed.

SUMMARY OF THE INVENTION

The present invention provides methods and compositions for ameliorating or preventing chronic allograft rejection in a human or animal allograft recipient. In an embodiment, the method comprises administering to an allograft recipient a therapeutically effective amount of cyclosporin in combination with a therapeutically effective amount of 2-chlorodeoxyadenosine. In an embodiment, advantageously for ease in administration, the cyclosporin and the 2-chloro-deoxyadenosine are combined with at least one pharmaceutically acceptable excipient in a single composition. In specific embodiments, the composition is administered subcutaneously, orally, or intravenously.

The present invention also provides a composition suitable for treating chronic allograft rejection. In one embodiment, the composition comprises a therapeutically effective amount of cyclosporin in combination with a therapeutically effective amount of 2-chlorodeoxyadenosine and a pharmaceutically acceptable excipient. In one embodiment, the composition contains an amount of cyclosporin that is about 7 to about 224 times the amount by weight of 2-chlorodeoxyadenosine.

Further the present invention provides for a method of ameliorating chronic allograft rejection by administering an amount of CSA and 2-CDA effective sufficient to suppress the B-cell mediated response to an allograft. In one embodiment, the allograft organ is a heart and the B-cell mediated response is one or a combination of mononuclear cell infiltration in the myocardium, myocardial fibrosis, and intimal proliferation of smooth muscle cells.

DETAILED DESCRIPTION OF THE PREFERRED EMBODIMENTS

Figure 1:
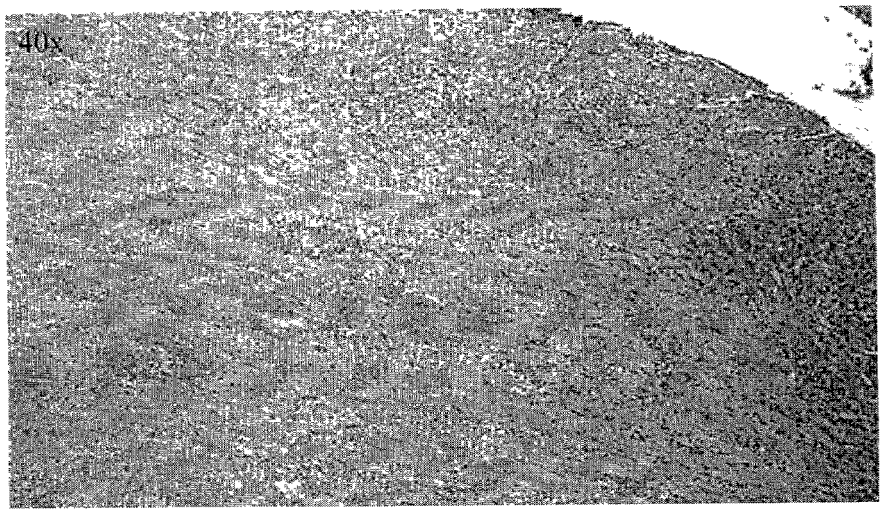
FIG. 1 shows a 40× photomicrograph of a cross section of the myocardium of a heart transplanted from a ACI strain rat donor to a LEW ("Lewis") strain rat host 90 days post transplant; the recipient received 5 mg CSA per kilogram of body mass per day for two weeks and 5 mg CSA per kg three times per week until sacrifice at 90 days post transplant.

One embodiment provides a method comprising administering to an allograft recipient a therapeutically effective amount of cyclosporin in combination with a therapeutically effective amount of 2-chlorodeoxyadenosine. In an embodiment, advantageously for ease in administration, the cyclosporin and the 2-chloro-deoxyadenosine are combined with at least one pharmaceutically acceptable excipient in a single pharmaceutical composition.

The pharmaceutical compositions employed in the methods of this invention can be administered to humans and other animals orally, rectally, parenterally (i.e., intravenously, intramuscularly, or subcutaneously), intracistemally, intravaginally, intraperitoneally, topically (as by powders, ointments, or drops), bucally, or as an oral or nasal spray. In specific embodiments, the composition is administered subcutaneously, orally, or intravenously Pharmaceutical compositions for use in the methods of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

If desired and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alignates, gelatin, polyvinyl-pyrrolidone, sucrose, and acacia, c) humectants such as glycerol, d) disintegrating agents such as agar-agar, calcium carbonate, potato ortapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in sort and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite agar-agar, and tragacanth, and mixtures thereof.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

In one embodiment, dosage levels are about 0.1 to about 200 mg of active compound per kilogram of body weight per day are administered orally to a mammalian patient. In another embodiment, dosage levels of about 0.5 to about 150 mg of active compound per kilogram of body weight per day are administered orally to a mammalian patient. In further embodiment, dosage levels of about 1 to about 125 mg of active compound per kilogram of body weight per day are administered orally to a mammalian patient. If desired, the effective daily dose may be divided into multiple doses for purposes of administration, e.g., two to four separate doses per day.

In general, the amount of cyclosporin administered is about 2 to about 224 times the amount by weight of 2-chlorodeoxyadenosine administered. Suitably the amount of cyclosporin administered is about 7 to about 112 mg per kilogram of allograft body mass per week. The dosage of 2-chlorodeoxyadenosine is suitably about 0.5 to about 3.0 mg per kilogram of allograft recipient body mass per week. In another embodiment, the dosage of 2-chlorodeoxyadenosine is about 1.0 mg to about 16 mg per kilogram of allograft recipient body mass per day. In illustrative embodiments, cyclosporin is administered at a dose of about 7 to about 112 mg per kilogram of recipient body mass per week.

In one embodiment, the therapeutically effective amount of 2-chlorodeoxyadenosine is between about 0.5 mg and about 3 mg per kilogram of recipient body mass per week. Suitably, the dose of 2-chlorodeoxyadenosine is about 1 mg per kilogram of recipient body mass per week, divided into one or more doses per week. In another embodiment, about 1.5 mg of 2-chlorodeoxyadenosine per kilogram of allograft recipient body mass is administered about every three weeks in one or more doses. In another embodiment, about 3 mg of 2-chlorodeoxyadenosine per kilogram of allograft recipient body mass is administered about every three weeks in one or more doses.

In one embodiment, cyclosporin is administered in a regime of about 5 mg per kilogram of recipient body mass per day for about two weeks followed by about 5 mg per kilogram of recipient body mass about three times per week. In such a dosage regime, the daily dose can be suitably divided into at least two equal daily doses.

EXAMPLE 1

Effect of Treatment on White Blood Cell Populations

We have briefly summarized the histological findings of the appearance of transplanted hearts in the Lewis to F344 rat model (Cramer, D. V., et al., *Transplantation Proceedings*, 29:616 (1997) incorporated herein in its entirety. Further studies, described below, have examined the effects of concomitant treatment of CSA and 2-CDA on circulating numbers of T cells.

Tables 1-5 present data regarding the numbers of T-cells, and the CD4+ and CD8+T-cell subsets, in untreated Lewis rats (control), and treated F344 rats that had received a transplanted Lewis rat heart after 14 days and 90 days of treatment with various combinations of CSA and 2-CDA. Treatment Group 1 rats were treated with the combination of 2.5 mg/kg/day CSA and 0.1 mg/kg/day 2-CDA. Treatment Group 2 rats were treated with the combination of 5 mg/kg/day CSA and 0.1 mg/kg/day 2-CDA. Treatment Group 3 rats were treated with a combination of 5 mg/kg/day CSA and 1 mg/kg/day 2-CDA.

| KEY TO TREATMENT GROUPS | | |
|---|---|---|
| Control (untreated Lewis Rats) = 1 | | |
| Experimental Treatments | 14 Day | 90 Day |
| Group 1: 2.5 mg/kg/day CSA + 0.1 mg/kg/day 2-CDA | 2 | 3 |
| Group 2: 5 mg/kg/day CSA + 0.1 mg/kg/day 2-CDA | 4 | 5 |
| Group 3: 5 mg/kg/day CSA + 1 mg/kg/day 2-CDA | 6 | 7 |

The significance of the effect of the treatment regimes on the measured parameters was evaluated using a t-test; the results of the analysis are presented in Table 6, below. The treatment regime administered to Group 3 (see Key, above) produced a significant reduction at both 14 days and 90 days in number of lymph cells, number of CD4+ cells and number of T-cells, as compared to the untreated control animals. A significant reduction in CD4+ cells is also seen at 14 days with Group 2. The reduction in CD4+ cells in Group 2 at 90 days and in Group 1 at 90 days does not reach the P=0.05 level (0.065 and 0.067, respectfully), perhaps due to the smaller sample sizes.

Previous studies using this animal transplantation model have been predictive of the efficacy of immunosuppressive therapies in humans (e.g. CSA, mycophenolate mofetil, rapamycin, CTLA-4). Thus, CSA-based immunosuppression with chronic 2CDA administration is expected to prolong graft survival in humans. This therapy will increase the efficacy of immunosuppression in ongoing, low grade rejection by safely enhancing the overall level of immunosuppression, specifically targeting macrophage and antibody/B-Cell mediated mechanisms of injury more effectively than current therapies.

TABLE 1

The effect of CSA + 2-CDA on T cells and CD4, CD8 T cell subsets
Control (Untreated Lewis Rats)

| Animal ID | Days Post-Tx | Total W.B cells/mm3 | % lymph | # lymph cells/mm$^3$ | % CD4 | # CD4 cells/mm$^3$ | % CD8 | # CD8 cells/mm$^3$ | % T cells | # T cells/mm$^3$ | CD4/CD8 | % HCT |
|---|---|---|---|---|---|---|---|---|---|---|---|---|
| L1 | 0 | 12600 | 54 | 6804 | 57.7 | 3925 | 20.9 | 1422 | 76.8 | 5225 | 2.7 | — |
| L2 | 0 | 6000 | 62 | 3720 | 61.2 | 2276 | 16.5 | 613 | 84.8 | 3150 | 3.7 | — |
| L3 | 0 | 13850 | 60 | 8100 | 66.0 | 5346 | 27.0 | 2236 | 85.0 | 6880 | 2.4 | — |
| L4 | 0 | 14450 | 57 | 8236 | 62.8 | 5173 | 24.6 | 2026 | 85.0 | 7001 | 2.55 | — |
| L5 | 0 | 6000 | 42 | 2520 | 66.5 | 1675 | 24.9 | 627 | 78.6 | 1981 | 2.67 | — |
| L6 | 0 | 5800 | 30 | 1740 | 53.7 | 934 | 23.4 | 407 | 82.1 | 1428 | 2.3 | 44 |
| L7 | 0 | 8800 | 44 | 3872 | 54.0 | 2091 | 28.4 | 1100 | 77.1 | 2985 | 1.9 | 40 |
| L8 | 0 | 13900 | 42 | 5838 | 56.9 | 3322 | 19.3 | 1127 | 77.3 | 4513 | 2.95 | 46 |
| L9 | 0 | 11900 | 35 | 4165 | 61.3 | 2553 | 15.3 | 637 | 85.1 | 3544 | 4.01 | 41 |
| L10 | 0 | 18500 | — | — | 61.6 | — | 23.5 | — | 89.1 | — | 2.62 | — |
| L11 | 0 | 13200 | — | — | 42.2 | — | 10.2 | — | 69.3 | — | 4.14 | — |
| L12 | 0 | 5100 | — | — | 52.9 | — | 22.7 | — | 71.6 | — | 2.33 | 42 |
| L13 | 0 | 8700 | 54 | 4698 | 57.6 | 2706 | 12.7 | 597 | 79.8 | 3749 | 4.54 | 53 |

TABLE 2

The effect of CSA + 2-CDA on T cells and CD4, CD8 T cell subsets
GROUP 1: 2.5 mg/kg/day CSA + 0.1 mg/kg/day 2-CDA

| Animal ID | Days Post-Tx | Total W.B cells/mm$^3$ | % lymph | # lymph cells/mm$^3$ | % CD4 | # CD4 cells/mm$^3$ | % CD8 | # CD8 cells/mm$^3$ | % T cells | # T cells/mm$^3$ | CD4/CD8 | % HCT |
|---|---|---|---|---|---|---|---|---|---|---|---|---|
| F1* | 14 | 7350 | 65 | 4777 | 56.5 | 2698 | 34.4 | 1643 | 81.2 | 3877 | 1.64 | — |
| F2 | 14 | 6700 | 60 | 4020 | 55.6 | 2235 | 32.6 | 1310 | 77.6 | 3119 | 1.71 | — |
| F3 | 14 | 11000 | 42 | 4620 | 49.0 | 2264 | 36.7 | 1695 | 72.3 | 3340 | 1.33 | — |

TABLE 2-continued

The effect of CSA + 2-CDA on T cells and CD4, CD8 T cell subsets
GROUP 1: 2.5 mg/kg/day CSA + 0.1 mg/kg/day 2-CDA

| Animal ID | Days Post-Tx | Total W.B cells/mm$^3$ | % lymph | # lymph cells/mm$^3$ | % CD4 | # CD4 cells/mm$^3$ | % CD8 | # CD8 cells/mm$^3$ | % T cells | # T cells/mm$^3$ | CD4/CD8 | % HCT |
|---|---|---|---|---|---|---|---|---|---|---|---|---|
| F4 | 14 | 10000 | 40 | 4000 | 48.6 | 1944 | 39.0 | 1501 | 68.5 | 2700 | 1.24 | — |
| F5 | 14 | 5350 | 62 | 3317 | 50.3 | 1668 | 37.9 | 1257 | 70.5 | 2339 | 1.33 | — |
| F1REJ | 22 | 9550 | 36 | 3582 | 55.7 | 1995 | 29.8 | 1067 | 83.3 | 2984 | 1.87 | 38 |
| F2REJ | 28 | 9900 | 46 | 4554 | 64.4 | 2932 | 22.6 | 1029 | 89.9 | 4094 | 2.8 | 43 |
| F2 | 90 | 7100 | 42 | 2982 | 42.8 | 1276 | 23.7 | 707 | 73.2 | 2183 | 1.8 | 43 |
| F3 | 90 | 5800 | 50 | 2900 | 43.6 | 1264 | 24.5 | 710 | 69.0 | 2001 | 1.78 | 43 |
| F4 | 90 | 8600 | 32 | 2752 | 42.3 | 1164 | 25.5 | 702 | 66.7 | 1836 | 1.66 | 45 |

TABLE 3

The effect of CSA + 2-CDA on T cells and CD4, CD8 T cell subsets
GROUP 2: 5 mg/kg/day CSA + 0.1 mg/kg/day 2-CDA

| Animal ID | Days Post-Tx | Total W.B cells/mm$^3$ | % lymph | # lymph cells/mm$^3$ | % CD4 | # CD4 cells/mm$^3$ | # CD8 | % CD8 cells/mm$^3$ | % T cells | # T cells/mm$^3$ | CD4/CD8 | % HCT |
|---|---|---|---|---|---|---|---|---|---|---|---|---|
| F6+ | 14 | 12500 | 50 | 6250 | 32.2 | 2012 | 20.7 | 1293 | 58.1 | 3631 | 1.55 | 40 |
| F9+ | 14 | 13000 | 37 | 4810 | 44.9 | 2159 | 24.6 | 1183 | 68.6 | 3299 | 1.82 | 34 |
| F10+ | 14 | 11100 | 41 | 4551 | 39.4 | 1793 | 22.5 | 1123 | 59.0 | 2685 | 1.75 | 35 |
| F11+ | 14 | 11800 | 35 | 4130 | 32.7 | 1350 | 25.1 | 1036 | 60.3 | 2490 | 1.3 | 41 |
| F12+ | 14 | 9200 | 33 | 3036 | 39.5 | 1199 | 18.9 | 574 | 73.1 | 2189 | 2.09 | 39 |
| F13 | 14 | 10300 | 35 | 3605 | 44.2 | 1593 | 27.3 | 984 | 73.1 | 2635 | 1.62 | 37 |
| *F6 | 90 | 15400 | 35 | 5390 | NA | NA | NA | NA | NA | NA | NA | — |
| *F10 | 90 | 11400 | 45 | 5130 | NA | NA | NA | NA | NA | NA | NA | — |
| F11 | 90 | 6300 | 49 | 3087 | 41.8 | 1290 | 8.9 | 275 | 72.6 | 2242 | 4.69 | — |
| F12 | 90 | 7700 | 45 | 3465 | 38.2 | 1324 | 11.2 | 388 | 72.2 | 2502 | 3.41 | — |
| F13 | 90 | 5000 | 50 | 2500 | 45.6 | 1140 | 13.1 | 328 | 76.9 | 1923 | 3.48 | — |

NA = Not Available

TABLE 4

The effect of CSA + 2-CDA on T cells and CD4, CD8 T cell subsets
GROUP 3: 5 mg/kg/day CSA + 1 mg/kg/day 2-CDA

| Animal ID | Days Post-Tx | Total W.B cells/mm$^3$ | % lymph | # lymph cells/mm$^3$ | % CD4 | # CD4 cells/mm$^3$ | % CD8 | # CD8 cells/mm$^3$ | % T cells | # T cells/mm$^3$ | CD4/CD8 | % HCT |
|---|---|---|---|---|---|---|---|---|---|---|---|---|
| F18 | 14 | 5300 | 26 | 1378 | 54 | 744 | 28.9 | 398 | 66.2 | 912 | 1.87 | 43 |
| F19 | 14 | 6500 | 36 | 2340 | 53.1 | 1243 | 28 | 655 | 64.2 | 1502 | 1.89 | 43 |
| F20+ | 14 | 6700 | 27 | 1809 | 47.2 | 854 | 23.4 | 423 | 58.2 | 1053 | 2.02 | 43 |
| F21+ | 14 | 6000 | 22 | 1320 | 54.5 | 719 | 29.6 | 391 | 61.3 | 809 | 1.84 | 40 |
| F19 | 90 | 8700 | 56 | 2296 | 35.2 | 808 | 16.6 | 381 | 54.1 | 1242 | 2.12 | 45 |
| F20 | 90 | 4100 | 49 | 1470 | 34.6 | 509 | 15.6 | 229 | 48.3 | 710 | 2.21 | 43 |
| *F21 | 90 | 2500 | 57 | 1425 | 34.8 | 496 | 17 | 242 | 50.8 | 724 | 2.05 | 25 |

*Blood clotted

TABLE 5

The effect of CSA + 2-CDA on T cells and CD4, CD8 T cell subsets
Summary [Mean ± S.E.M. (N)]

| Key | | Total W.B cells/mm$^3$ | % Lymph | # Lymph cells/mm$^3$ | % CD4 | # CD4 cells/mm$^3$ | % CD8 | # CD8 cells/mm$^3$ | # T cells | # T cells/mm$^3$ | CD4/CD8 |
|---|---|---|---|---|---|---|---|---|---|---|---|
| 1 | Naive Lewis | 10,677 ± 4,218 (13) | 48 ± 11 (10) | 4969 ± 2234 (13) | 58 ± 6.5 (10) | 3000 ± 1447 (13) | 20.7 ± 5.6 (10) | 1079.2 ± 637.4 (13) | 80.1 ± 5.7 (10) | 4045.6 ± 1878.5 (10) | 3.0 ± 0.8 (10) |
| 2 | Group #1 14 da | 8,080 ± 2,351 (5) | 53.8 ± 11.8 (5) | 4146.8 ± 580.4 (5) | 52 ± 3.8 (5) | 2162 ± 386 (5) | 36.1 ± 2.6 (5) | 1481 ± 195 (5) | 74.0 ± 5.3 (5) | 3075 ± 591 (5) | 1.45 ± 0.21 (5) |
| 3 | Group #1 90 da | 7,167 ± 1,401 (3) | 41.3 ± 9.0 (3) | 2878 ± 116.6 (3) | 42.9 ± 0.7 (3) | 2135 ± 62 (3) | 24.6 ± 0.9 (3) | 706 ± 4 (3) | 69.6 ± 3.3 (3) | 2007 ± 174 (3) | 1.75 ± 0.08 (3) |
| 4 | Group #2 14 da | 11,3177 ± 1,416 (6) | 38.5 ± 6.3 (6) | 4397 ± 1112 (6) | 38.8 ± 5.4 (6) | 1684 ± 374 (6) | 23.2 ± 3.1 (6) | 1032 ± 250 (6) | 65.2 ± 6.8 (6) | 2822 ± 538 (6) | 1.69 ± 0.27 (6) |

TABLE 5-continued

The effect of CSA + 2-CDA on T cells and CD4, CD8 T cell subsets
Summary [Mean ± S.E.M. (N)]

| Key | | Total W.B cells/mm$^3$ | % Lymph | # Lymph cells/mm$^3$ | % CD4 | # CD4 cells/mm$^3$ | % CD8 | # CD8 cells/mm$^3$ | # T cells | # T cells/mm$^3$ | CD4/ CD8 |
|---|---|---|---|---|---|---|---|---|---|---|---|
| 5 | Group #2 90 da | 9160 ± 4230 (5) | 44.8 ± 5.9 (5) | 3914 ± 1279 (5) | 41.9 ± 3.7 (3) | 1251 ± 97.9 (3) | 11.1 ± 2.1 (3) | 330 ± 56.5 (3) | 73.9 ± 2.6 (3) | 2222 ± 290 (3) | 3.86 ± 0.72 (3) |
| 6 | Group #3 14 da | 6125 ± 624 (4) | 27.8 ± 5.9 (4) | 1712 ± 472 (4) | 52.2 ± 3.4 (4) | 890 ± 243 (4) | 27.5 ± 2.8 (4) | 467 ± 126 (4) | 62.5 ± 3.5 (4) | 1069 ± 306 (4) | 1.91 ± 0.08 (4) |
| 7 | Group #3 90 da | 5100 ± 3219 (3) | 54 ± 4.4 (3) | 1730 ± 490 (3) | 34.9 ± 0.3 (3) | 604 ± 177 (3) | 16.4 ± 0.7 (3) | 284 ± 84 (3) | 51.1 ± 2.9 (3) | 892 ± 303 (3) | 2.1 ± 0.1 (3) |

TABLE 6

Summary of t-Test Results

| | Control vs. Group 1 14 day | | Control vs. Group 1 90 day | | Control vs. Group 2 14 day | | Control vs. Group 2 90 day | | Control vs. Group 3 14 day | | Control vs. Group 3 90 day |
|---|---|---|---|---|---|---|---|---|---|---|---|
| WB Cell | | | | | | | | | | | |
| T value | 1.286 | T value | 1.391 | T value | −0.357 | T value | 0.683 | T value | 2.104 | T value | 2.129 |
| P value | 0.217 | P value | 0.186 | P value | 0.725 | P value | 0.504 | P value | 0.052 | P value | 0.051 |
| D.F. | 16 | D.F. | 14 | D.F. | 17 | D.F. | 16 | D.F. | 15 | D.F. | 14 |
| Mean Lymph No. | | | | | | | | | | | |
| T value | 0.800 | T value | 1.580 | T value | 0.582 | T value | 0.972 | T value | 2.838 | T value | 2.433 |
| P value | 0.438 | P value | 0.143 | P value | 0.570 | P value | 0.349 | P value | 0.015 | P value | 0.033 |
| D.F. | 13 | D.F. | 11 | D.F. | 14 | D.F. | 13 | D.F. | 12 | D.F. | 11 |
| Mean CD4 No. | | | | | | | | | | | |
| T value | 1.251 | T value | 2.049 | T value | 2.156 | T value | 2.029 | T value | 2.833 | T value | 2.775 |
| P value | 0.238 | P value | 0.065 | P value | 0.049 | P value | 0.067 | P value | 0.015 | P value | 0.018 |
| D.F. | 13 | D.F. | 11 | D.F. | 14 | D.F. | 11 | D.F. | 12 | D.F. | 11 |
| Mean CD8 No. | | | | | | | | | | | |
| T value | −1.356 | T value | 0.982 | T value | 0.171 | T value | 1.971 | T value | 1.863 | T value | 2.091 |
| P value | 0.198 | P value | 0.347 | P value | 0.867 | P value | 0.074 | P value | 0.087 | P value | 0.060 |
| D.F. | 13 | D.F. | 11 | D.F. | 14 | D.F. | 11 | D.F. | 12 | D.F. | 11 |
| Mean T-cell No. | | | | | | | | | | | |
| T value | 1.110 | T value | 1.821 | T value | 1.539 | T value | 1.626 | T value | 3.079 | T value | 2.811 |
| P value | 0.287 | P value | 0.095 | P value | 0.146 | P value | 0.132 | P value | 0.01 | P value | 0.016 |
| D.F. | 13 | D.F. | 11 | D.F. | 14 | D.F. | 11 | D.F. | 12 | D.F. | 11 |

D.F: Degrees of Freedom

EXAMPLE 2

An ACI-LEW rat cardiac transplant model was used to test the ability of 2-CDA to suppress allograft chronic rejection.

| Group | Treatment Regimen |
|---|---|
| A | CSA dosage finding group |
| B | 5/mg/kg/day CSA; 1-14 days, then 3 times per week for 90 days |
| C | 1 mg/kg/week 2-CDA Di for 90 days plus 5/mg/kg/day CSA |
| D | 1 mg/kg 2-CDA on days 3, 4, 5, 23, 24, 25, 43, 44, 45, 63, 64, 65, 83, 84 and 85 days post transplant, plus 5/mg/kg/day CSA |
| E | 0.5 mg/kg 2-CDA on days 3, 4, 5, 23, 24, 25, 43, 44, 45, 63, 64, 65, 83, 84 and 85 days post transplant, plus 5/mg/kg/day CSA |

Animals were sacrificed at 90 days post transplant. Heart grafts were subjected to evaluation which included the quantification of the extent to which the following pathologies typically associated with chronic allograft rejection were present in the allograft models: myocardial Infiltration (MI), myocardial fibrosis (MF), and intimal proliferation (IP).

Each of these pathologies is associated with the vascular disease of transplant arteriosclerosis. Tables 7 and 8, below, summarize the findings.

TABLE 7

Summary of Histological Findings

| Group | N | Histological Score* MI | MF | IP |
|---|---|---|---|---|
| A | 4 | ++++ | + | +++ |
| B | 4 | +++ | + | +++ |
| C | 4 | + | − | + |
| D | 4 | ++ | + | +++ |
| E | 4 | ++ | + | +++ |

*Histological scores represent average grade scores within a group.

TABLE 8

Results of Quantitative Analysis of Myocardial Inflammatory Infiltrates

| Group | N | Infiltrates/mm$^2$ Mean ± SD | P Value* |
|---|---|---|---|
| B | 4 | 4197.7; 3465.1; 3613.9; 3359.5 (3595.4 ± 404.6) | — |
| C | 4 | 1291.0; 3069.12; 1132.89; 1545.0 (1759.5 ± 889.5) | 0.0077 |
| D | 4 | 2942.0; 3444.89; 2894.3; 2842.3 (3030.9 ± 278.9) | 0.0359 |
| E | 4 | 2978.1; 3207.9; 2345.2; 2796.1 (2831.8 ± 365.6) | 0.0195 |

*T-test for independent samples. All the groups are compared with Control Group.

Figure 2:
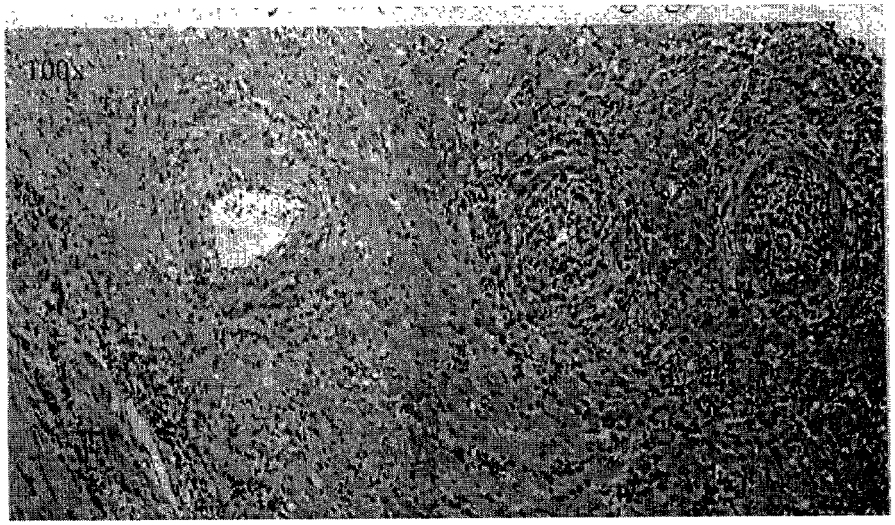
FIG. 2 shows 100× photomicrographs of cross sections of different fields of the myocardium shown in FIG. 1.
Figure 3:
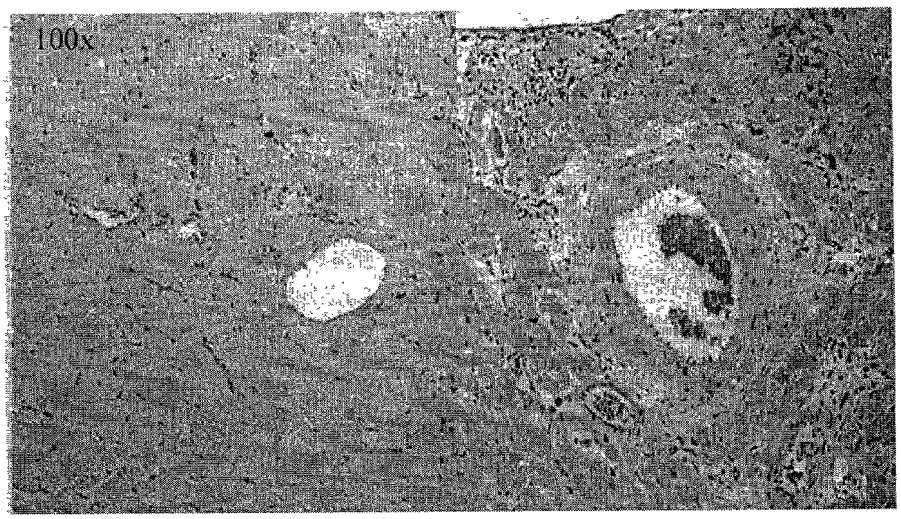
FIG. 3 shows 100× photomicrographs of cross sections of the myocardium of a ACI to LEW rat cardiac transplant 90 days post transplant; the recipient received 5 mg CSA per kilogram of body mass per day for two weeks and 5 mg CSA per kg three times per week thereafter, and 2-CDA at 1 mg/kg per week, until sacrifice at 90 days post transplant.
Figure 4:
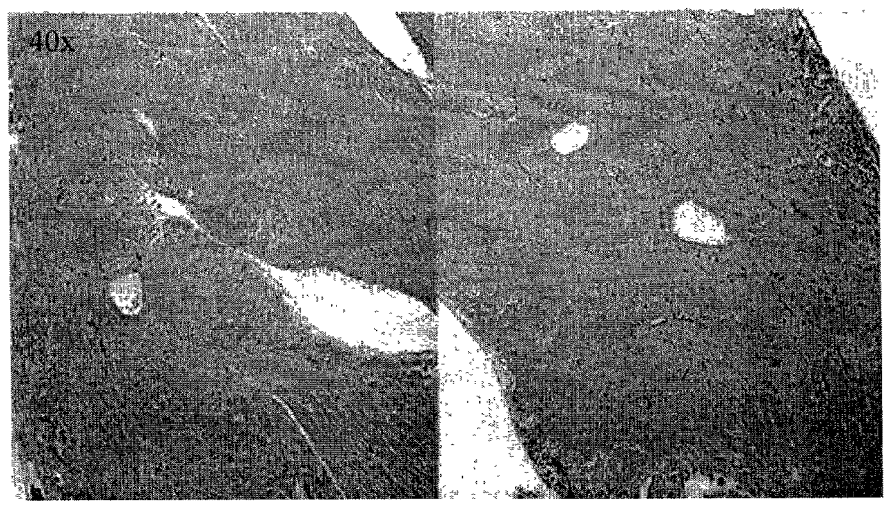
FIG. 4 shows 40× photomicrographs of cross sections of different fields of the myocardium shown in FIG. 5.
Figure 5:
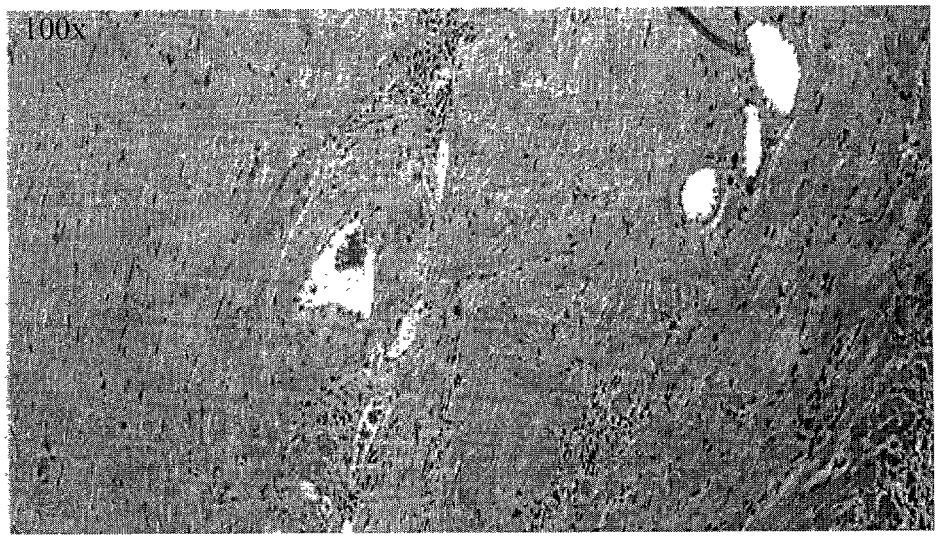
FIG. 5 shows 100× photomicrographs of cross sections of the myocardium of a ACI to LEW rat cardiac transplant 90 days post transplant; the recipient received 5 mg CSA per kilogram of body mass per day for two weeks and 5 mg CSA per kg three times per week thereafter, and 2-CDA at 1 mg/kg per week, until sacrifice at 90 post transplant.
Figure 6:
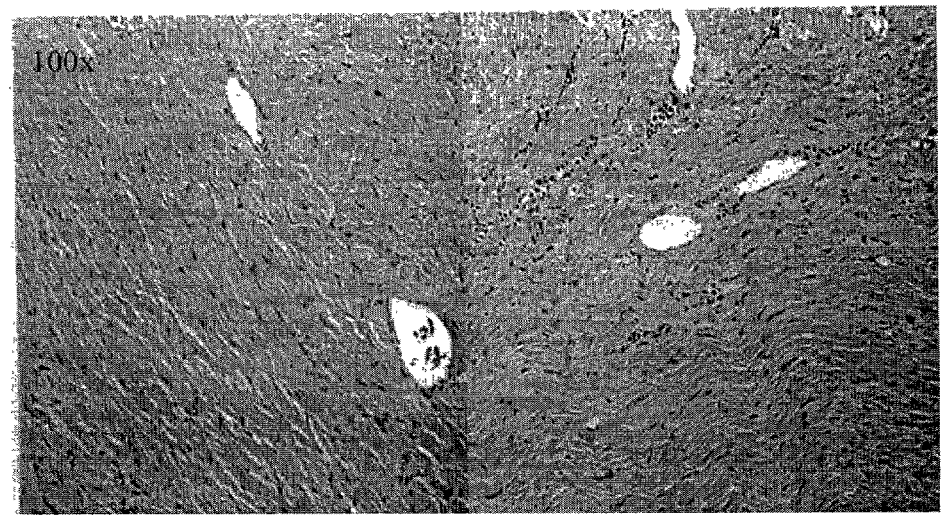
FIG. 6 shows 100× photomicrographs of cross sections of different fields of the myocardium shown in FIG. 5.
Figure 7:
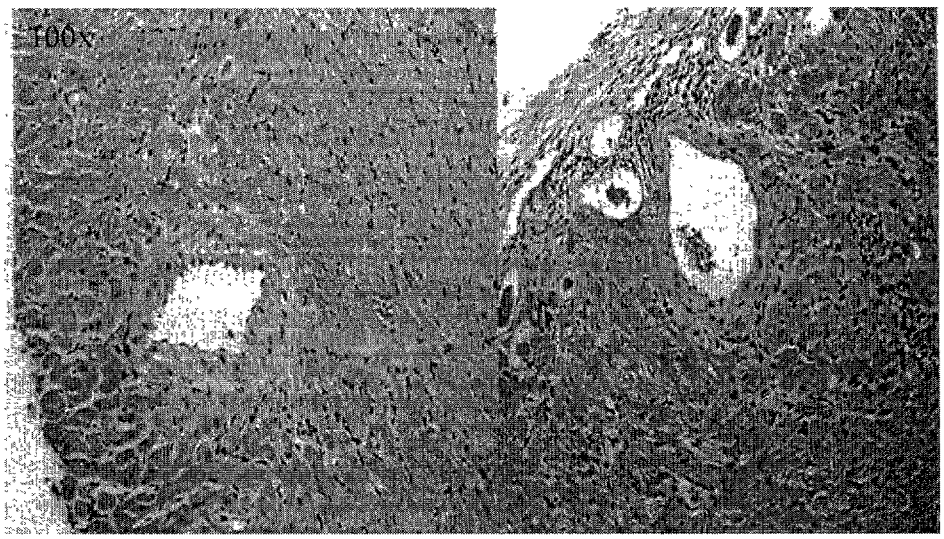
FIG. 7 shows 100× photomicrographs of cross sections of the myocardium of a ACI to LEW rat cardiac transplant 90 days post transplant; the recipient received 5 mg CSA per kilogram of body mass per day for two weeks and 5 mg CSA per kg three times per week thereafter, and 2-CDA at 1 mg/kg per week, until sacrifice at 90 days post transplant.
Figure 8:
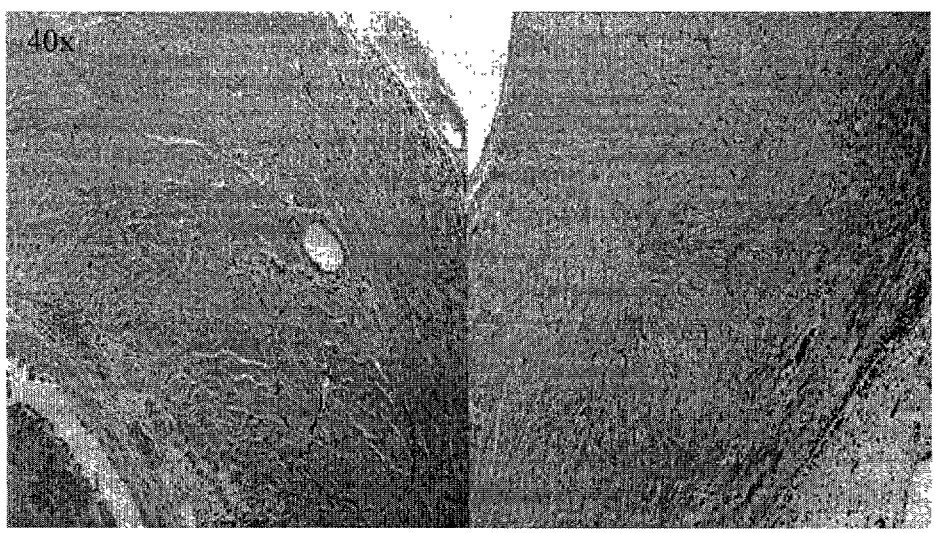
FIG. 8 shows 40× photomicrographs of cross sections of different fields of the myocardium shown in FIG. 7.

FIGS. 1 and 2 show photomicrographs of the myocardium of one of the animals in Group B showing that animals treated with CSA alone displayed a histological picture consistent with severe chronic rejection, including intensive mononuclear cell infiltration in the myocardium and prominent vascular lesions of transplant arteriosclerosis.

In comparison, FIGS. 3, 4, 5, 6, 7 and 8 show photomicrographs of the myocardium of three animals from group C that had been treated with 5 mg/kg/day CSA for two weeks and 5 mg/kg three times per week thereafter, and 1 mg/kg/wk 2-CDA, demonstrate only mild lymphocyte infiltration in the myocardium and very limited development of transplant arteriosclerosis. One animal in Group C showed moderate to severe chronic rejection in the heart graft. The condition of the grafted heart deteriorated at 60 days post transplant.

The results obtained in Groups D and E indicate that relative effectiveness of administration of 2-CDA by interval dosing schedules compared to a single weekly dose.

These studies provide evidence of efficacy the present invention for concomitant use of CSA based immunosuppression with chronic 2CDA administration to prevent chronic vascular rejection after vascularized organ transplantation. The test animals tolerated the therapy with no deaths or obvious complications.

These results show that an effective amount of CSA was about 5 mg per kilogram of allograft recipient body mass per day for two weeks and then about 5 mg per kilogram of recipient body mass three times per week thereafter.

In general, actual dosage levels of active ingredients in the pharmaceutical compositions of this invention may be varied so as to obtain an amount of the active compounds that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. In general, an initial starting point for comparable human dosage of CSA can be obtained from a 1994 survey of U.S. transplant centers: 9±3 mg/kg/day (mean ±S.D.) for renal transplant patients, 8±4 mg/kg/day for liver transplant patients and 7±3 mg/kg/day for heart transplant patients. Physicians Desk Reference, 52nd Edition, pp. 1882-1890, at 1887 (1998). Accordingly, for humans, a starting approximate CSA dosage range is about 1 mg to about 16 mg per kilogram of recipient body mass per day. On a weekly basis, the dosage is in the range of about 7 to about 112 mg/kg per week. If desired, the effective daily dose may be divided into multiple doses for purposes of administration, e.g., two to four separate doses per day.

The present study found that the most effective dose of 2-CDA was 1 mg per kilogram of recipient body mass per week. Other effective doses included of 0.5 and 1.0 mg/kg at days 3-5, 23-25, 43-45, 63-65 and 83-85 post transplant ("PTX"). These doses are in the range of about 1.5-3 mg/kg of recipient body mass every three weeks, or about 0.5 to 1.0 mg/kg/wk. Accordingly, it can be shown that effective dosages of CSA may range from about 2 to about 224 times the amount of 2-CDA. As noted above, one skilled in the art will be able to readily adjust the 2-CDA dosage in relation to a human patient's CSA dosage to obtain the desired therapeutic effect.

EXAMPLE 3

A human trial of the use of CSA in combination with 2-CDA in human kidney transplanted patients involves a randomized, prospective, non-blinded study of 150 patients. Over a two year period, 100 patients receive 2-CDA in combination with CSA while 50 patients receive other immunosuppression controls. 2-CDA is administered weekly at a dosage based upon clinical trials involving 2-CDA for the treatment of multiple sclerosis and rheumatoid arthritis. Dosage can be administered subcutaneously or orally. Concomitant immunosuppression with cyclosporin is administered. Control patients are placed on or maintained on cyclosporin and prednisone therapy at doses determined as optimal for each patient based upon known protocols.

Change in renal function is measured over two years including graft loss and endpoint. Serial serum creatine levels every 3 months and slope of creatine as mg/dl/month are measured. Serial 24 hour unine collections for creatine clearance and protein excretion are measured every six months. Initial and final biopsies are examined and graded by the Banff 1997 Pathology Scheme for interstitial fibrosis, arteriolar changes and glomerular sclerosis. Additional measurements include blood counts and T-cell profiles (CD4/CD8).

While the foregoing is intended to be illustrative of the present invention, the scope is defined by the appended claims. Numerous variations and modifications may be effected without departing from the true spirit and scope of the invention.

We claim:

1. A method of treating chronic allograft rejection in an allograft recipient in need of such treatment comprising administering cyclosporin A and 2-chlorodeoxyadenosine to the allograft recipient in a coordinated dosage regime comprising days on which both cyclosporin A and 2-chlorodeoxyadenosine are administered and days on which only cyclosporin A is administered, wherein the coordinated dosage regime comprises administration of 2-chlorodeoxyadenosine in one or more doses over a period of three weeks, and administration of cyclosporin A in at least two equal daily doses per week for a period of three weeks; and repeating the coordinated dosage regime over a treatment period of at least 90 days.

2. The method according to claim 1 wherein about one to about 16 milligrams of cyclosporin A per kilogram of recipient body mass per day and about 0.5 to about 3 milligrams of 2-chlorodeoxyadenosine per kilogram of recipient body mass per week is administered.

3. The method according to claim 1 wherein the dosing regime for cyclosporin A is between about 7 and about 112 mg per kilogram of recipient body mass per week.

4. The method according to claim 1 wherein the dosing regime for cyclosporin A is about 5 mg per kilogram of recipient body mass per day for about two weeks followed by about 5 mg per kilogram of recipient body mass about three times per week.

5. The method according to claim 1 wherein the dosing regime for 2-chlorodeoxyadenosine is a single dose administered about once per week.

6. The method according to claim 1 wherein the dosing regime for 2-chlorodeoxyadenosine is a daily dose administered for 1 day to 3 consecutive days during a period of about 7 to about 21 days.

7. The method according to claim 1 wherein the dosing regime for 2-chlorodeoxyadenosine is about 1.5 to about 3 mg per kilogram of recipient body mass per three weeks.

8. The method according to claim 1 wherein the mode of administration of cyclosporin A and 2-chlorodeoxyadenosine is subcutaneously, orally, or intravenously.

9. The method according to claim 1 wherein the dosing regime comprises administration of cyclosporin A in at least three doses per week and administration of 2-chlorodeoxyadenosine in a once a week dose.

10. The method according to claim 1 wherein the dosing regime comprises administration of cyclosporin A in at least three doses per week and administration of 2-chlorodeoxyadenosine in at least three doses over a period of three weeks.

11. The method according to claim 10 wherein the dosing regime comprises administration of cyclosporin A in at least three doses per week and administration of 2-chlorodeoxyadenosine in an interval of three consecutive daily doses once every three weeks.

* * * * *